United States Patent [19]

Ukigaya et al.

[11] Patent Number: 4,692,337

[45] Date of Patent: Sep. 8, 1987

[54] SUSTAINED RELEASE PHARMACEUTICAL TABLET OF THEOPHYLLINE AND PRODUCTION PROCESS THEREOF

[75] Inventors: Tadashi Ukigaya; Keizaburo Ogawa, both of Kawagoe, Japan

[73] Assignee: Nikken Chemicals Co., Ltd., Tokyo, Japan

[21] Appl. No.: 655,738

[22] Filed: Sep. 28, 1984

[30] Foreign Application Priority Data

Apr. 9, 1983 [JP] Japan .................................. 58-61524

[51] Int. Cl.$^4$ ......................... A61K 9/26; A61K 31/52
[52] U.S. Cl. ..................................... 424/469; 514/263
[58] Field of Search ............................... 514/263, 781; 424/19-22, 35

[56] References Cited

U.S. PATENT DOCUMENTS

| | | | |
|---|---|---|---|
| 2,980,589 | 4/1961 | de Grunigen | 514/781 |
| 3,079,303 | 2/1963 | Raff et al. | 424/35 |
| 3,860,733 | 1/1975 | Morse et al. | 424/35 |
| 3,950,508 | 4/1976 | Mony et al. | 514/960 |
| 4,085,214 | 4/1978 | Higuchi et al. | 514/263 |
| 4,261,970 | 4/1981 | Ogawa et al. | 424/19 |
| 4,348,397 | 9/1982 | May et al. | 514/562 |
| 4,361,545 | 11/1982 | Powell et al. | 424/19 |
| 4,368,197 | 1/1983 | Shefter et al. | 514/186 |
| 4,369,172 | 1/1983 | Schor et al. | 514/781 |
| 4,461,759 | 7/1984 | Dunn | 424/35 |
| 4,465,660 | 8/1984 | David et al. | 424/15 |
| 4,547,358 | 10/1985 | David et al. | 424/14 |
| 4,590,062 | 5/1986 | Jang | 424/19 |

Primary Examiner—Shep K. Rose
Attorney, Agent, or Firm—Finnegan, Henderson, Farabow, Garrett & Dunner

[57] ABSTRACT

A sustained release pharmaceutical tablet comprising theophylline and ethyl cellulose uniformly dispersed therein in an amount of 5 to 200 parts by weight of ethyl cellulose based on 100 parts by weight of the theophylline, the hardness of the tablet being 0.5 to 16.0 kg. This sustained release pharmaceutical tablet can be prepared by uniformly mixing 100 parts by weight of theophylline and 5 to 200 parts by weight of ethyl cellulose, and compression molding the resultant mixture by a direct compression method to form a tablet.

2 Claims, 1 Drawing Figure

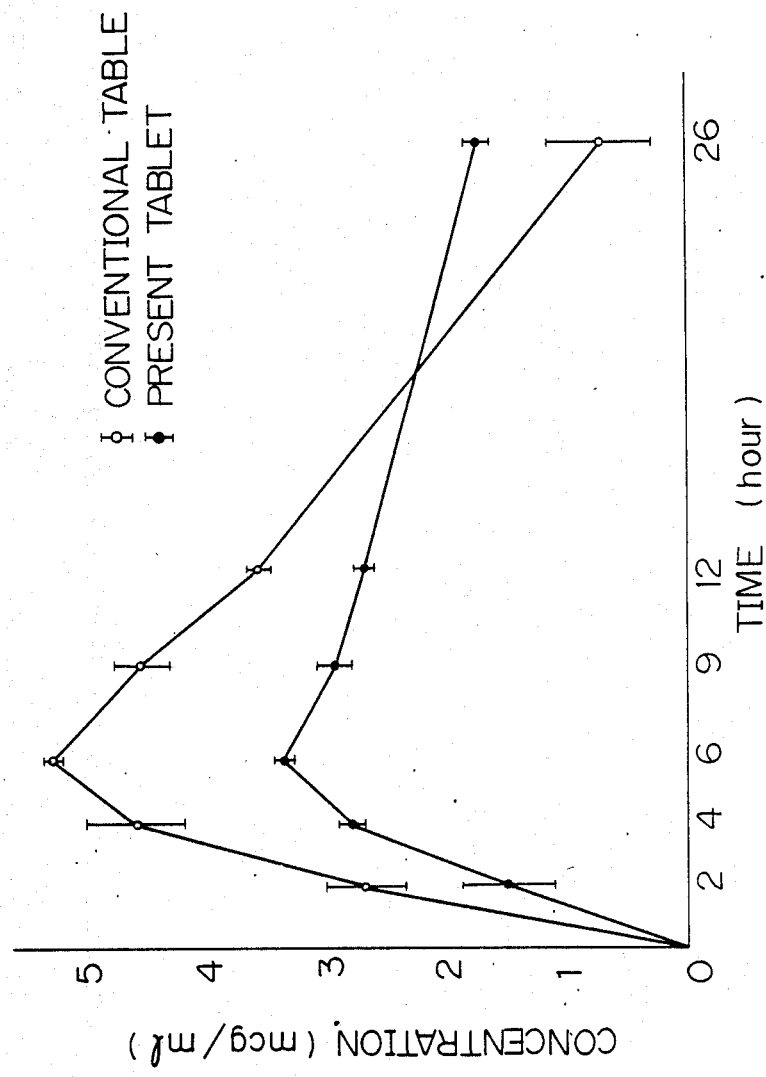

SUSTAINED RELEASE PHARMACEUTICAL TABLET OF THEOPHYLLINE AND PRODUCTION PROCESS THEREOF

BACKGROUND OF THE INVENTION

1. Field of the Invention

The present invention relates to a sustained release pharmaceutical tablet of theophylline and a production process thereof. More specifically, it relates to a sustained release pharmaceutical tablet of theophylline containing a specified ratio of theophylline and ethyl cellulose and being prepared by a direct compression molding method.

2. Description of Prior Art

Theophylline is widely used as an effective medicament for therapy and prevention of bronchial asthma. The dosage of theophylline, however, must be strictly controlled, as is known in the art. This is because theophylline has a narrow range of effective concentration in blood (i.e., 5 to 20 $\mu$g/ml) and gives rise to side-effects at the blood concentration (i.e., 25 $\mu$g/ml or more) close to the range of effective blood concentration. These side effects include headaches, nausea and arrhythmia. Further, the biological half-life of theophylline is relatively short (i.e., about 6 hours). Theophylline must therefore be administered four times a day (i.e., every 6 hours) to maintain its effective concentration in the blood. Such a frequent dosage is very troublesome to patients. Also due to the short-half life, sufficient effect against asthma attack before dawn, the prime period for such attacks cannot be expected by theophylline administration before going to bed.

Various attempts have been made to develop sustained release theophylline pharmaceutical preparations to overcome the above problems. Several preparations have been proposed or marketed heretofore.

For example, U.S. Pat. Nos. 3,062,720, 3,402,240, and 3,456,049 disclose sustained, slow, or gradual release preparations or medicinal tablets comprising medicaments dispersed in matrices composed of substantially water-insoluble or slightly water-soluble fatty materials or waxes. U.S. Pat. Nos. 3,080,294, 3,109,775, 3,344,029, and 3,872,998 and Japanese Unexamined Patent Publication (Kokai) No. 56-122311 disclose sustained release pharmaceutical preparations comprising medicaments, in the form of beads having different release speeds, encapsuled in pellets, tablets, or capsules. Furthermore, U.S. Pat. Nos. 3,039,933, 3,322,633, and 3,632,739 disclose sustained release pharmaceutical tablets in which ethyl cellulose is contained as a portion of a matrix component, although the use of theophylline is not taught in these patent specifications.

Although these proposed sustained release preparations of theophylline alleviate the trouble in administration of theophylline, they do not eliminate it completely. That is, these sustained release theophylline preparations have an effective duration of 8 to 12 hours. Therefore, chronic bronchial asthmatic patients must still take these theophylline preparations two or three times a day in order to maintain the effective blood concentration. While better than that of conventional i.e., non-sustained release type theophylline preparations, this frequency is still greater than desired for chronic patients.

The above-mentioned preparations utilizing a water-insoluble (or slightly water-soluble) matrix still have disadvantages in that the weight percentage of the carrier or vehicle is as large as 50% or more. Thus, the size of the tablets inevitably becomes large in the case of a medicament, such as theophylline, which must be administered in a large dose. Also, the control of the release speed of the medicament is not necessarily easy since, depending upon the types or combinations of the matrix substances, the rate rapidly decreases with the lapse of time after administration.

Furthermore, the above-mentioned preparations utilizing coated beads (or small powder particles) also have disadvantages in that highly skilled art and complicated operations are required for the production of the coated beads, which cause high production costs.

Recently, a new type of a sustained release tablet of theophylline has been proposed in Japanese Unexamined Patent Publication (Kokai) No. 57-112322 (corresponding to U.S. patent application Ser. No. 147429 filed May 6, 1980). This proposed tablet comprises 95% to 99.8% by weight of theophylline in the form of a thin non-disintegration type flat plate. This tablet is advantageous in that its production is simple and it contains a large amount of the effective ingredient. It is still disadvantageous, however, in that a small sized tablet containing a small content (e.g., 50 to 150 mg) of theophylline has insufficient strength and too fast a release speed of the effective ingredient. Thus, a desired theophylline tablet having satisfactory sustained release properties and sufficient strength cannot be expected.

SUMMARY OF THE INVENTION

Accordingly, a main object of the present invention is to eliminate the above-mentioned disadvantages of the prior art and to provide a sustained release tablet of theophylline capable of providing stable effective blood concentration of the theophylline for 12 to 24 hours when administered once or twice a day.

Another object of the present invention is to provide a small sized and readily applicable sustained release pharmaceutical tablet of theophylline having a relatively high theophylline content.

A further object of the present invention is to provide a sustained release pharmaceutical tablet of theophylline having a consistent quality and capable of being readily produced.

In accordance with the present invention, there is provided a sustained release pharmaceutical tablet comprising theophylline and ethyl cellulose uniformly dispersed therein in an amount of 5 to 200 parts by weight of ethyl cellulose, based on 100 parts by weight of the theophylline, the hardness of the tablet being 0.5 to 16.0 kg.

In accordance with the present invention, there is also provided a process for producing a sustained release pharmaceutical tablet of theophylline comprising the steps of: uniformly mixing 100 parts by weight of theophylline and 5 to 200 parts by weight of ethyl cellulose; and compression molding the resultant mixture by a direct compression method to form a tablet.

BRIEF DESCRIPTION OF THE DRAWING

The present invention will be better understood from the description set forth below with reference to the drawing, in which FIG. 1 is a graph showing the changes with the lapse of time in the theophylline blood concentrations in human of a conventional sustained release tablet and the tablet prepared in Example 3 according to the present invention.

DESCRIPTION OF THE PREFERRED EMBODIMENTS

As mentioned above, according to the present invention, the desired sustained release pharmaceutical tablet of theophylline can be prepared by uniformly mixing theophylline and ethyl cellulose in a weight ratio of theophylline: ethyl cellulose of 100:5 to 200, preferably 100:10 to 100, and, optionally after mixing a small amount of a lubricant, compression molding the resultant mixture by a direct compression method. Thus, a sustained release pharmaceutical tablet having a desired size can be produced.

The theophylline usable in the present invention can be any commercially available product in the form of, for example, powder. The powdered theophylline can be directly used in the production of the desired tablet according to the present invention or used or after being appropriately crushed, ground, or milled.

The ethyl celluloses usable in the present invention are those which are compatible with theophylline. Any commercially available ethyl cellulose may be appropriately used. Examples of such commercially available products are "Ethocel" Standard or Medium (manufactured by Dow Chemical Co., Ltd.) Fine divided products thereof having a size of 20 mesh or less are preferably used, 32 mesh or less being more preferably used.

The release (or dissolution) speed of theophylline in the sustained release theophylline tablet according to the present invention can be readily controlled by changing the mixing amount of the ethyl cellulose to theophylline. Generally speaking, the release speed decreases as the mixing amount of the ethyl cellulose is increased. The release speed of theophylline can also be controlled by changing the hardness of the tablet. Generally, the release speed of theophylline decreases with an increase in the hardness of the tablet.

The mixing amount of the ethyl cellulose in the present invention must be 5 to 200 parts by weight, preferably 10 to 100 parts by weight, based on 100 parts by weight of the theophylline. A mixing amount of the ethyl cellulose of less than the above-specified range results in too fast a release speed of theophylline, which does not provide the desired sustained release effect of theophylline. Contrary to this, a mixing amount of the ethyl cellulose of more than the above-specified range causes insufficient release of the theophylline, which does not provide sufficient medicinal effect.

Furthermore, as mentioned above, while the sustained release theophylline tablet according to the present invention, substantially comprises the mixture of the specified amounts of theophylline and ethyl cellulose, it can optionally contain conventional ingredients such as an excipient or a lubricant in such an amount that the release speed of the theophylline is not adversely affected.

Examples of an excipient are lactose, sucrose, glucose, mannitol, and crystalline cellulose (e.g., "Avicel"). Examples of the lubricants usable at the occasion of the tableting are magnesium stearate, calcium stearate, light silicic anhydride (e.g., "Carplex" manufactured by Shionogi & Co., Ltd.), and "Aerosil" (manufactured by Nippon Aerosil Co.).

As mentioned above, according to the present invention, the desired sustained release tablet of theophylline can be prepared by directly compression molding a uniform mixture of the specified ratio of theophylline and ethyl cellulose. This direct compression method is very advantageous compared with other conventional tablet molding methods as intermediate steps, such as a granulating step, can be omitted and the production operation is very simple. Thus, the production process of the sustained release theophylline tablet according to be present invention is very time-saving and economical.

The resultant sustained release theophylline tablet according to the present invention has a hardness of 0.5 to 16.0 kg as determined by a Kiya hardness tester (manufactured by KIYA SEISAKUSHO LTD.).

According to the present invention, the ethyl cellulose also functions as an excipitant and, therefore, the use of other excipients is not generally required. For this reason, the tablet can be formed in the form of a very small size compared with conventional tablet. A typical size of the sustained release theophylline tablet of the present invention is approximately 5 to 10 mm in diameter and 2.0 to 4.6 mm in thickness. Thus, the sustained release theophylline tablet of the present invention is advantageous in that it can be orally administered very easily.

Furthermore, the sustained release theophylline tablet according to the present invention very gradually and substantially completely releases the theophylline. Accordingly, when the sustained release theophylline tablet according to the present invention is orally administered to a patient, there is no excess increase in the theophylline blood concentration immediately after administration, which is usually observed in the case of a conventional tablets, and the effective theophylline blood concentration can be stably maintained 12 to 24 hours after the optimum theophylline content in blood is attained. Consequently, the dosage frequency can be advantageously decreased to once or twice a day when the present theophylline tablet is used.

As already mentioned hereinbefore, the theophylline blood concentration of 5 to 20 $\mu$g/ml must be maintained in order to aquire therapeutic effect in the treatment of bronchial asthma. Accordingly, when the present theophylline tablet is used for this purpose, tablets in an amount of 500 to 800 mg in terms of theophylline (e.g., 2 to 4 tablets containing 200 mg of the theophylline) are orally administered once or twice a day.

EXAMPLES

The present invention will now be further illustrated in detail by, but is by no means limited to, the following examples.

EXAMPLE 1 (PREPARATION EXAMPLE)

A 10 g amount of theophylline, 8 g of ethyl cellulose (i.e., "Ethocel Standard 10" manufactured by Dow Chemical Co., Ltd.), 0.36 g of calcium stearate, and 0.09 g of light silicic anhydride (i.e., "Carplex" manufactured by Shionogi & Co., Ltd.) were charged in a vessel. The mixture was thoroughly mixed by a Micro V-type mixer (Tsutsui Rikagaku Kikai Co., Ltd.) to prepare a uniform mixture.

The mixture was compression molded by a Rotary Tabloid Machine (HT-9, Hata Iron Works). Thus, theophylline tablets having a weight of 184.5 mg, a diameter of 8 mm, and a thickness of 4 mm were obtained.

EXAMPLE 2 (PREPARATION EXAMPLE)

Theophylline tablets having a weight of 164 mg, a diameter of 7 mm, and a thickness of 3.8 mm were prepared in the same manner as in Example 1 from 10 g of theophylline, 6 g of ethyl cellulose (i.e., "Ethocel Standard 100" manufactured by Dow Chemical Co., Ltd.), 0.32 g of calcium stearate, and 0.08 g of light silicic anhydride used in Example 1.

EXAMPLE 3 (PREPARATION EXAMPLE)

Theophylline tablets having a weight of 82 mg, a diameter of 6 mm, and a thickness of 2.4 mm were prepared in the same manner as in Example 1 from 10 g of theophylline, 6 g of ethyl cellulose used in Example 2, 0.32 g of magnesium stearate, and 0.08 g of light silicic anhydride used in Example 1.

EXAMPLE 4 (PREPARATION EXAMPLE)

Theophylline tablets having a weight of 184.5 mg, a diameter of 8 mm, and a thickness of 3.8 mm were prepared in the same manner as in Example 1 from 30 g of theophylline, 6 g of ethyl cellulose used in Example 1, 0.72 g of calcium stearate, and 0.18 g of light silicic anhydride used in Example 1.

EXAMPLE 5 (PREPARATION EXAMPLE)

Theophylline tablets having a weight of 71.75 mg, a diameter of 5 mm, and a thickness of 3.7 mm were prepared in the same manner as in Example 1 from 50 g of theophylline, 20 g ethyl cellulose used in Example 2, 1.4 g of magnesium stearate, and 0.35 g of light silicic anhydride used in Exampel 1.

EXAMPLE 6 (PREPARATION EXAMPLE)

Theophylline tablets having a weight of 252.8 mg, a diameter of 8 mm, and a thickness of 4.6 mm were prepared in the same manner as in Example 1 from 60 g of theophylline, 12 g of ethyl cellulose used in Example 1, 1.44 g of calcium stearate, and 0.36 g of light silicic anhydride used in Example 1.

EXAMPLE 7 (PREPARATION EXAMPLE)

Theophylline tablets having a weight of 350.6 mg, a diameter of 10 mm, and a thickness of 4.3 mm were prepared in the same manner as in Example 1 from 90 g theophylline, 12 g of ethyl cellulose used in Example 1, 2.04 g of calcium stearate, and 0.51 g of light silicic anhydride used in Example 1.

EXAMPLE 8 (RELEASE TEST)

The tablets prepared in Examples 1 to 5 above were evaluated, in terms of the theophylline release (or dissolution) rate, according to the second method of dissolution test procedure (i.e., a Paddle method, 100 r.p.m.) defined in the Pharmacopoeia of Japen (Tenth eddition). The tablets were dissolved in the first and the second test solutions defined in the Pharmacopoeia of Japan to make the test solution, and the test solution was collected with time.

The dissolved amounts of theophylline in each test solution were determined by measuring the absorbance at 270 nm.

The results are shown in Table 1.

TABLE 1

| Test Solution | Dissolution Time (hr) | Theophylline Dissolution Rate (%) Example | | | | |
|---|---|---|---|---|---|---|
| | | 1 | 2 | 3 | 4 | 5 |
| I*1 | 1 | 24.3 | 24.2 | 32.2 | 25.8 | 37.8 |
| II*2 | 2 | 36.7 | 38.5 | 41.9 | 43.5 | 52.7 |
| II*2 | 4 | 52.6 | 57.4 | 53.6 | 65.6 | 67.1 |
| II*2 | 6 | 68.8 | 72.2 | 62.4 | 84.6 | 79.8 |
| II*2 | 8 | 83.0 | 86.3 | 70.4 | 95.4 | 91.0 |

TABLE 1-continued

| Test Solution | Dissolution Time (hr) | Theophylline Dissolution Rate (%) Example | | | | |
|---|---|---|---|---|---|---|
| | | 1 | 2 | 3 | 4 | 5 |
| II*2 | 10 | 95.2 | 98.0 | 77.3 | 99.8 | 98.9 |

*1 The first test solution defined in the Pharmacopoeia of Japan containing NaCl and dil. HCl (pH = 1.2).
*2 The second test solution defined in the Pharmacopoeia of Japan containing $KH_2PO_4$ and NaOH (pH = 6.8).

EXAMPLE 9 (APPLICATION EXAMPLE)

The transitional changes of the theophylline contents in human blood of the theophylline tablets prepared in Example 2 above and a conventional sustained release theophylline tablet containing 100 mg of theophtylline were evaluated by a random cross-over method.

Two grains of the sample tablets were administered to five healthy adult males having an age of 33 to 52 (38.4 on average) and a body weight of 51 to 68 kg (59.4 kg on average). The above-mentioned two types of the sample tablets were alternately administered with a withdrawal period for a week between the first and second administrations of the two samples. The test persons were prohibited from ingesting to obtain xanthin-containing food and beverages such as tea, coffee and cola from 12 hours before the administration to the end of the test period. Blood samples were taken before the administration (i.e., 0 hour) and 2, 4, 6, 9, 12, and 26 hours after the administration. The serum was separated from the sampled blood and stored in a frozen condition until determination.

The theophylline content in the blood was determined by measuring the absorbance at 280 nm by means of high speed liquid chromatography.

The results are shown in Table 2 and FIG. 1.

As clear from the results shown in Table 2 and FIG. 1, the variation of the theophylline concentration in blood of the present tablet was small and the desired theophylline concentration in blood was maintained for a long time (between 2 to 26 hours), compared with the conventional sustained release theophylline tablet.

TABLE 2

| Tablet | Test person | Time (hour) | | | | | |
|---|---|---|---|---|---|---|---|
| | | 0 | 2 | 4 | 6 | 9 | 12 | 26 |
| Control (conventional tablet) | A | ND | 3.1 | 4.8 | 5.2 | 4.2 | 3.6 | 1.7 |
| | B | ND | 2.9 | 5.2 | 5.3 | 4.3 | 3.8 | 1.9 |
| | C | ND | 2.5 | 4.2 | 5.3 | 4.2 | 3.5 | ND |
| | D | ND | 3.5 | 5.4 | 5.5 | 4.8 | 3.4 | ND |
| | E | ND | 1.5 | 3.2 | 5.2 | 5.4 | 3.7 | ND |
| | Average | — | 2.70 | 4.56 | 5.30 | 4.58 | 3.60 | 0.72 |
| | S E | — | 0.34 | 0.40 | 0.05 | 0.23 | 0.07 | 0.44 |
| Tablet of Example 3 | A | ND | ND | 2.6 | 3.4 | 2.7 | 2.9 | 1.7 |
| | B | ND | 1.8 | 2.8 | 3.4 | 3.0 | 2.6 | 1.9 |
| | C | ND | 1.8 | 2.5 | 3.5 | 3.1 | 2.7 | 2.0 |
| | D | ND | 2.3 | 2.9 | 3.2 | 2.6 | 2.5 | 1.6 |
| | E | ND | 1.6 | 3.0 | 3.5 | 3.4 | 2.8 | 1.5 |
| | Average | — | 1.50 | 2.76 | 3.40 | 2.96 | 2.70 | 1.74 |
| | S E | — | 0.39 | 0.09 | 0.05 | 0.14 | 0.07 | 0.09 |

(unit: mcg/ml)
ND: less than 0.5 mcg/ml

We claim:
1. A sustained release tablet consisting essentially of theophylline and ethyl cellulose produced by uniformly mixing together said theophylline and ethyl cellulose in an amount of 5 to 200 parts by weight of ethyl cellulose based on 100 parts by weight of the theophylline, and thereafter directly compressing the mixture into tablets having a hardness of from 0.5 to 16.0 kg.
2. The sustained release tablet of claim 1, wherein the amount of the ethyl cellulose is 10 to 100 parts by weight based on 100 parts by weight of the theophylline.

* * * * *

UNITED STATES PATENT AND TRADEMARK OFFICE
CERTIFICATE OF CORRECTION

PATENT NO. : 4,692,337

DATED : September 8, 1987

INVENTOR(S) : Tadashi Ukigaya et al.

It is certified that error appears in the above-identified patent and that said Letters Patent is hereby corrected as shown below:

Title page:

[30] Foreign Application Priority Data

Apr. 9, 1983 [JP]  Japan ..........58-61524
should be deleted from the Letters Patent.

Signed and Sealed this

Twelfth Day of July, 1988

Attest:

DONALD J. QUIGG

*Attesting Officer*   *Commissioner of Patents and Trademarks*